United States Patent [19]

Boberski et al.

[11] 4,174,228

[45] Nov. 13, 1979

[54] CEMENTITIOUS MAGNESIA COMPOSITIONS CONTAINING SALTS OF ORGANO-SILANOLS

[75] Inventors: William G. Boberski; Wen-Hsuan Chang, both of Gibsonia; Jerome A. Seiner, Pittsburgh, all of Pa.

[73] Assignee: PPG Industries, Inc., Pittsburgh, Pa.

[21] Appl. No.: 891,109

[22] Filed: Mar. 28, 1978

[51] Int. Cl.$^2$ ............................ C04B 9/02; C04B 9/04
[52] U.S. Cl. .................................. 106/107; 106/18.12; 106/18.21; 106/105; 106/108; 106/194; 106/203; 106/287.11; 106/287.13; 106/287.16; 260/29.6 S; 260/42.13
[58] Field of Search ............ 106/106, 107, 108, 287.11, 106/287.13, 287.15, 287.16, 194, 203, 204, 105; 260/29.6 S, 42.13

[56] References Cited

U.S. PATENT DOCUMENTS

| | | | |
|---|---|---|---|
| 2,905,562 | 9/1959 | Brown | 106/12 |
| 3,046,242 | 7/1962 | Santelli | 106/287.12 |
| 3,353,975 | 11/1967 | Shannon et al. | 106/107 |
| 3,499,955 | 3/1970 | Shannon | 106/106 |
| 3,753,750 | 8/1973 | Davis | 106/107 |

*Primary Examiner*—Lorenzo B. Hayes
*Attorney, Agent, or Firm*—Charles R. Wilson

[57] ABSTRACT

Magnesium oxide cementitious compositions are disclosed containing salts of organo-silanols. The silanol salts are water-soluble and are characterized in having attached to the silicon atom at least one group comprising a moiety attached to the silicon atom through a substantially non-hydrolyzable silicon-carbon bond and at least one silanol group which is at least partially neutralized with a base. A magnesia composition containing one or more of these organo-silanol salts has improved casting, molding, or spraying properties, as compared to a magnesia composition lacking the silanol salt.

66 Claims, 2 Drawing Figures

CEMENTITIOUS MAGNESIA COMPOSITIONS CONTAINING SALTS OF ORGANO-SILANOLS

BACKGROUND OF THE INVENTION

1. Field of the Invention

Cementitious magnesia compositions containing mixtures of magnesium oxide and other magnesium salts, such as magnesium chloride, and having organo-silicon compounds as viscosity reducing additives, are disclosed in copending U.S. application Ser. No. 891,110 filed on even date herewith and incorporated herein by reference. The present invention is directed to cementitious magnesia compositions containing organo-silanol salts as viscosity modifiers.

2. Description of the Prior Art

There is increasing demand for inexpensive, non-polluting molding and casting compounds as substitutes for scarce petroleum-derived molding materials, and for sprayable fire-proof insulating materials to replace carcinogenic asbestos-containing compositions. Widespread use of magnesium oxide (magnesia) cementitious compositions as substitutes in various molding, casting and spraying applications has been limited by the rather high viscosities of the compositions. The aforementioned copending application discloses organo-silicon compounds (organo-silanes) which have proved to be quite useful in reducing viscosities of magnesia compositions. The reduction in viscosity obtained by addition of certain organo-silanes to "high solids" magnesia compositions is advantageous inasmuch as there occurs no appreciable increase in composition volume that typically results from addition of water as a diluent to reduce viscosity, so that shrinkage of the composition upon curing is minimized. Moreover, with the absence of increased amounts of water as a viscosity reducer, the magnesia compositions do not require substantial increases in curing time and are less likely to aid in corrosion of a substrate.

There have been found some disadvantages, however, in use of certain organo-silane compounds having hydrolyzable groups attached to the silicon atom as viscosity reducing agents. For example, a typically useful organo-silane such as γ-aminopropyltriethoxysilane forms ethanol as a hydrolysis product in the presence of water in a magnesia composition. Other silanes having hydrolyzable organic radicals on the silicon atom may generate hydrolyzates which can be toxic, odorous, volatile or otherwise undesirable. Also, the silane can hydrolyze in the presence of a small amount of water to form undesirable and useless hydrolyzates; hence, care must be taken to ensure that the organo-silane is stored in a hermetically sealed container and that water vapor is prevented from entering the container when it is opened to remove a portion of the silane.

SUMMARY OF THE INVENTION

It has now been found that improved materials for molding, casting or spraying purposes may be provided by a cementitious composition comprising (a) magnesium oxide, (b) a magnesium salt having at least moderate solubility in water, (c) at least one water-soluble organo-silanol, a portion of which is at least partially neutralized with a base to provide a water-soluble product, and (d) a liquid phase comprising water in an amount effective to cause reaction of at least a portion of the magnesium oxide and at least a portion of the magnesium salt to form a matrix curable to a hardened state, wherein the cementitious composition exhibits a lower viscosity in its stage of initial application in a mold or as sprayed onto a substrate, than if the organo-silanol salt were absent. The water-soluble, base-neutralized organosilanol is typically characterized as a salt in that attached to its silicon atom is at least one silanol group which is at least partially neutralized with a base. A base-neutralized salt group attached to the silicon atom may be represented by the general formula $-O^-A^+$, wherein $A^+$ is typically a monovalent cation or one equivalent of a polyvalent cation. The organo-silanol salt is further characterized in having at least one group comprising a moiety that is attached to the silicon atom through a substantially non-hydrolyzable silicon-carbon bond. In further description of the invention, the term "organo moiety" is generally intended to mean that portion of the group attached to the silicon atom by a silicon-carbon bond, which portion is not substantially hydrolyzable at the silicon-carbon bond. Typical organo-silanol salts useful in the invention are characterizable in having an organo moiety attached to the silicon atom comprising groups which impart to the moiety a solubility property measurable by a working parameter of solubility. This parameter is relatable to observed decreases in viscosities during application uses of wet magnesia compositions containing the specified organo-silanol salt, as compared with magnesia compositions lacking the organo-silanol salt.

Cementitious compositions having one or more silanol salts of the described type retain most of the advantages of magnesia compositions containing organo-silicon compound viscosity modifiers described in the aforementioned copending application Ser. No. 891,110, while having important additional advantages. One advantage is that since the silicon atom of a silanol salt is free of groups hydrolyzable at the silicon atom, or at least has fewer hydrolyzable groups at the silicon atom than the silicon atom of its corresponding silane, there are no, or at least fewer, undesirable hydrolyzates formed in the presence of water. Another advantage of the silanol salts is their water stability which allows the silanol salts to be stored in water with no detrimental effects on their usefulness. The silanol salts remain in the salt form, or ionize, and in either form the salts retain their usefulness as viscosity reducing agents when the magnesia compositions are prepared for use. Inasmuch as there is less likelihood of waste or of decrease in the efficacy of the viscosity reducing agent in its water-stable salt form, there is provided a significant economic advantage because these organic viscosity reducing agents, though typically present in relatively small amounts in cementitious compositions, are several times more expensive than the inorganic components of the magnesia compositions.

BRIEF DESCRIPTION OF THE DRAWINGS

The accompanying drawings, in which FIGS. 1 and 2 compare viscosity profile data of preferred "test" compositions of the invention having an organo-silanol salt additive as compared against "control" compositions lacking the additive, illustrate examples of working embodiments of the invention according to the best mode so far devised in the practical application of the principles thereof.

DESCRIPTION OF THE PREFERRED EMBODIMENTS

Typically, a magnesia cement comprises a matrix or binder which forms a three-dimensional system of alternating molecular units when the composition is in its solidified or cured form. The binder is derived from bringing together water, at least one magnesium salt having at least moderate solubility in water, and magnesium oxide. Magnesium salts having moderate solubility in water are intended in this context to be those compounds having solubilities greater than one part solute in 1000 parts solvent. The solubility of magnesium oxide by comparison is $6.2 \times 10^{-3}$ parts per 1000 parts water.

A magnesium salt having at least moderate solubility in water and having been demonstrated as providing suitable magnesia compositions is magnesium chloride hexahydrate; other preferred magnesium salts include magnesium nitrate hexahydrate, magnesium acetate tetrahydrate and magnesium bromide hexahydrate.

Other magnesium salts having at least moderate solubility in water and which are believed suitable for use in the magnesia compositions of the invention include magnesium acetate, magnesium orthoarsenite, magnesium benzoate, magnesium bromide, magnesium selenate, magnesium silicofluoride, magnesium stannide, magnesium sulphate, magnesium sulphate heptahydrate, magnesium sulphite, magnesium thiosulphate, magnesium thiotellurite, magnesium hypophosphite, magnesium salicylate, magnesium fluosilicate, magnesium fluosilicate hexahydrate, magnesium formate, magnesium iodate, magnesium iodide, magnesium iodide octahydrate, magnesium lactate, magnesium molybdate, magnesium nitrate dihydrate, magnesium nitrite trihydrate, magnesium chlorate, magnesium perchlorate hexahydrate, magnesium chloride, magnesium hydrogen citrate pentahydrate, magnesium cyanide and magnesium ferrocyanide.

It is intended that in place of any of the aforementioned magnesium salts there may be present in the cementitious composition the precursors of these salts, for example, the cementitious composition may contain magnesium hydroxide and hydrochloric acid, the reaction product of which provides a magnesium chloride salt. Thus, where the invention is defined as requiring a magnesium salt, this requirement may be satisfied by the presence in the cementitious composition of suitable precursors reactable to form the magnesium salt.

There may be, of course, more than one of the aforementioned water-soluble magnesium salts present in the composition in combination with the magnesium oxide. The total amount of all magnesium containing salts in the composition is preferred to be at least that amount which forms a saturated or nearly saturated solution in the water solvent, which compositions thus may be characterized as "high solids" compositions. Generally, the mole ratio of magnesium oxide to soluble magnesium salt is in the range of 3:1 to 10:1. Preferably, the mole ratio range is 6:1 to 7.5:1.

Water of any reasonable purity may be used in which to bring together the magnesium-containing components. The water should be free, however, of any contaminants which inhibit the curing of the cementitious composition or which tend to weaken the cured composition by reacting with constituents of the binder matrix; for example, strong acid species present in the water could react with basic components of the composition and generate heat which could accelerate cure, and could appreciably weaken the cured composition by attacking the inorganic salts of the matrix. Generally, commonly available tap water is suitable for use in formulation of the composition.

Generally, the amount of water utilized in the compositions is in a mole ratio range of water to magnesium salt of 8:1 to 30:1. Preferably, the mole ratio of water to magnesium salt ranges from 11:1 to 15:1.

The silanol salts useful in the invention are characterized in having attached to the silicon atom one, two or three salt groups comprising oxygen and a cation, with the salt group attached to the silicon atom through the oxygen atom, as represented by the idealized formula The portion of the salt group designated $A^+$ may be satisfied by a monovalent cation or one equivalent of a polyvalent cation. Also, there may be one cation shared by two silicon-attached oxygen atoms, such that the number of discrete salt groups per molecule may not be equal to a whole integer. The monovalent cation may be tertiary sulphonium, ammonium, substituted ammonium, quaternary ammonium, quaternary phosphonium, or any cation of the Group IA elements, other than hydrogen, which comprise the alkali metal group. Preferred cations include those of lithium, sodium and potassium. Suitable polyvalent cations include those of magnesium, calcium and polyammonium, with the proviso that the base-neutralized product be water-soluble.

The silanol salt is also characterized in having attached to its silicon atom at least one organic group comprising a moiety which is attached to the silicon atom through a substantially non-hydrolyzable silicon-carbon bond, which organic group moiety is designated as the "organo moiety" for purposes of defining the invention. Generally, a useful organo moiety may comprise an alkyl group which may be substituted with one or more chemical groups such as alkyl or alkyloxy of one to about eight carbon atoms, primary amino and secondary amino groups.

Where less than all of the chemically substitutable positions at the silicon atom consist of the aforementioned salt groups and organo moieties, there may be attached to the silicon atom one or two hydrolyzable groups. A suitable hydrolyzable group attached to the silicon atom may be alkoxyl, substituted alkoxyl, aryloxyl, substituted aryloxyl, aralkoxyl, substituted aralkoxyl, alkylamino, substituted alkylamino, silylamino, substituted silylamino, mercapto and substituted mercapto groups.

Examples of suitable alkoxyl groups include methoxy, ethoxy, propoxy, butoxy, acetoxy and the like. Suitable substituted alkoxyl groups include chloro, bromo and iodo β-substituted alkoxyl groups, where the alkoxyl moiety is of the aforementioned groups. Examples of suitable aryloxy, aralkoxy, substituted aryloxy and substituted aralkoxy groups are, respectively, phenoxy, phenylethoxy, chlorophenylethoxy and phenylchloroethoxy radicals. Suitable alkylamino and substituted alkylamino groups are, respectively, methylamino and dimethylamino. Examples of mercapto and substituted mercapto groups include, respectively, ethyl mercapto and chloroethyl mercapto groups.

Silylamino and substituted silylamino groups include those secondary and tertiary amine groups having a silicon atom bonded to the amino nitrogen.

Specific fully neutralized silanol salts which can be used to provide the aforementioned advantages associated with a reduction of viscosity in magnesia compositions include the potassium salt hydrolyzate of γ-aminopropyltriethoxysilane, depicted in idealized formula I:

(I)

and the potassium salt hydrolyzate of N-β-aminoethyl-γ-aminopropyltrimethoxysilane of idealized formula II:

(II)

These silanol salts of idealized formula I and II may be derived from the base hydrolysis of their respective organo-silicon compound precursors of formula III and IV, namely, γ-aminopropyltriethoxysilane (A-1100, Union Carbide):

(III)

and N-β-aminoethyl-γ-aminopropyltrimethoxysilane (A-1120; Union Carbide):

(IV)

These organo-silanol salts are derived from their organo-silane precursors by hydrolysis in the presence of a base containing one of the aforementioned monovalent cations, such as potassium hydroxide. Generally, an hydrolysis reaction occurs between an organo-silane having one or more hydrolyzable groups and an amount of base equivalent to the number of equivalents of hydrolyzable groups on the silane, with heat accelerating the hydrolysis reaction. It is to be appreciated that the idealized formulae I and II depict what is believed to be the major constituent of the potassium salt of the hydrolyzate of the corresponding silane. The salts formed from these and other silane hydrolyzates may actually comprise a mixture of compounds having one, two or three salt groups at the substitutable positions of the silicon atom, which mixture may also comprise minor amounts of hydrolyzate intermediate of the silanol salt, as well as linear and cyclic condensation products of the silanols such as linear or cyclic siloxanes.

It is expected that salts formed from the hydrolyzates of other organo-silicon compounds are also useful in the compositions of the invention. In the aforementioned co-pending application, magnesia compositions are disclosed having various organo-silicon compounds, which compositions have been shown to have improved spraying, molding or casting properties. The usefulness of these organo-silicon compounds in a magnesia composition has been shown to be related to a solubility property of a portion of the organo-silicon compound. Generally, the solubility of an organic species may be expressed by its solubility parameter, $\delta$, defined as

$$\delta = \frac{F}{V}$$

where F is a molar attraction constant of an organic species in (calories-cubic centimeters)$^{\frac{1}{2}}$ per mole and V is a molar volume constant of the species in cubic centimeters per mole. Where the organic species comprises one or more chemical groups, a parameter of solubility for the whole organic species may be calculated from the weighted average of the individual chemical groups. Where the constants listed in Table I are used for calculating this parameter of solubility, the result is designated a "working parameter of solubility", $\delta_{wp}$, which may be expressed as

$$\delta_{wp} = \frac{\Sigma F_i}{\Sigma V_i}$$

Surprisingly, there has been found a striking correlation between improvements in the casting, molding or spraying properties or magnesia compositions containing an organo-silicon compound that has at least one organo moiety attached to the silicon atom which is not hydrolyzable as the organo moiety-attaching silicon-carbon bond, where this organo moiety has a working parameter of solubility within a range of about 6.2 to about 8.0 (cal./c.c.)$^{\frac{1}{2}}$. This correlation has also been found valid for the organo-silanol salts depicted in formulae I and II.

Generally, the organo moiety not hydrolyzable at the silicon atom of the organo-silanol salt or the organo-silicon compound may comprise one or more groups selected from a large number of organic groups provided that the working parameter of solubility of the organo moiety is within the specified range. Families of groups from which useful moieties may be derived to provide a suitable value of the working parameter of solubility include alkyl, oxalkyl and azaalkyl, and alkenyl, oxalkenyl and azaalkenyl where the carbon-carbon unsaturation may be further reacted to provide epoxy or oxirane groups in the reactant group. Each of the aforementioned groups may be substituted with groups such as alkyl, alkoxy, aryl, aryloxy, substituted aryloxy, acrylyl, substituted acrylyl, carboxy, carboalkoxy, amino, amido, ureido, oxiranyl and sulphur. Typical examples of groups for making up the organo moiety include lower alkyl of one to ten carbon atoms; organic acid groups such as nitrogen-containing groups such as an epoxy containing group such as and a divalent thio group such as —SH and —SR, wherein R in each of the above specified groups may be hydrogen or some other low molecular weight group.

The working parameter of solubility values for the aforementioned and many other organic groups may be calculated from molar attraction and molar volume constants found in the literature. The values set forth in Table I, for example, are drawn from the considerable empirical and theoretical efforts of Bunn, Hoy and Van Krevelen verifying and expanding upon the earlier work of P. A. Small.

TABLE I

| Chemical Group | Molar Attraction Constant[a] $F_i[(cal\text{-}c.c.)^{\frac{1}{2}}/mole]$ | Molar Volume Constant[b] $V_i(c.c./mole)$ |
|---|---|---|
| —CH$_2$— | 131.5 | 21.8 |
| —CH$_3$ | 148.3 | 27.8 |
| $\diagdown$CH$\diagup$ | 86.0 | 13.6[d] |
| —NH$_2$ | 226.6 | 21.1[d] |
| —NH— | 180.0 | 14.6 |
| $\mid$ —N— | 61.1 | 8.7[d] |
| —OH | 225.8 | 14.9 |
| —O—(ether) | 115.0 | 7.3 |
| —⟨O⟩— | 735[c] | 89.9 |
| —CH=CH— | 222[c] | 16.9[d] |
| CH$_2$=CH— | 301[c] | 40.8[d] |
| —SH | 315[c] | 29.6[d] |
| —S— | 209.4 | 21.6[d] |
| $\mid$ —C=O | 263.0 | 21.6 |
| —COO— | 326.6 | 28.9 |
| —O—(epoxide) | 176.2 | 7.3 |
| $\overset{O}{\underset{\|}{—HNCO—}}$ | 506.6[e] | 43.5[e] |
| $\overset{O}{\underset{\|}{H_2NCO—}}$ | 553.2[e] | .50[e] |
| $\overset{O}{\underset{\|}{H_2NCNH—}}$ | 669.6[e] | 57.3[e] |
| $\overset{O}{\underset{\|}{—HNCNH—}}$ | 623[e] | 50.8[e] |
| $\overset{O}{\underset{\|}{—CNH_2}}$ | 489.6[e] | 42.7[e] |
| $\overset{O}{\underset{\|}{—CNH—}}$ | 443[e] | 36.2[e] |

[a]Values taken from Hoy, J.P.T., 42, 76 (1970), except where indicated.
[b]Values taken from Bunn, J. Poly, Sci., 16, 323 (1955), except where indicated.
[c]Values taken from Small, J. Appl. Chem., 3, 71 (1953).
[d]Values calculated by doubling corresponding molar volume values based on Van Der Waal energy calculations reported by Van Krevelen et al., Properties of Polymers, Elsevier Publishing Co., New York (1972) App. I.
[e]Values developed by adding constants listed in Table I for componenet portions of each composite chemical group.

Specific organo-silicon compounds are known which have at least one silicon-attached hydrolyzable group and at least one silicon-attached non-hydrolyzable moiety, where the moiety has a working parameter of solubility within the range of about 6.2 to about 8.0 (cal./c.c.)$^{\frac{1}{2}}$, from which suitable organo-silanol salts may be derived by base hydrolysis with at least partial neutralization of the organo-silanol. These organo-silicon compounds, known to provide magnesia compositions with improved molding, casting or spraying properties, include the silanes depicted in formula III and IV and four other commercially available compounds depicted in formulae V through VIII, namely γ-methacryloxypropyltrimethoxysilane (A-174; Union Carbide):

γ-glycidoxypropyltrimethoxysilane (A-187; Union Carbide):

γ-aminopropylmethyldiethoxysilane (Petrarch Systems):

and δ-aminobutyldimethylmethoxysilane (Silar Labs):

Other suitable organo-silicon compounds may be derived from the reaction of a silane having an organo moiety containing an epoxy group and a compound containing one or more chemical groups having an active hydrogen atom, such as amino, amide, ureido, urea, urethane, thiol, and hydroxyl groups, each having at least one active hydrogen. Or, the organo-silicon compound may be derived from the reaction of an epoxy-containing compound and a silane having an organo moiety containing groups having an active hydrogen atom, such as amines, amides, ureas, urethanes and thiols. The epoxy-containing compound may be an aliphatic epoxide such as 1,2-butylene oxide or it may be an aliphatic polyepoxide such as 1,4-butanediol diglycidyl ether.

Other suitable organo-silicon compounds may be derived from the reaction of a compound containing acrylyl or substituted acrylyl groups and a silane having an organo moiety comprising an amino group containing at least one active hydrogen. Or, suitable organo-silicon compounds may comprise the reaction products of an amino-compound having at least one active hydrogen and a silane having an organo moiety comprising acrylyl or substituted acrylyl groups.

Preferred organo-silicon compound reaction products may be derived from the reaction of aminoalkylsilanes, such as those illustrated in formulae III, IV, VII and VIII, with 1,2-butylene oxide. For example, the reaction of γ-aminopropyltriethoxysilane with 1,2-butylene oxide in varying molar ratios may provide a mixture comprising in varying amounts organo-silicon reaction products believed to have the structures depicted in formulae IX, X and XI, which mixture is suitable for use in cementitious compositions:

Another useful organo-silicon compound may be derived from reacting in approximately 2 to 1 molar ratio γ-aminopropyltriethoxysilane and 1,4-butanediol diglycidyl ether which provides a reaction product comprising a compound having two silicon atoms per molecule believed to have the structure depicted in formula XII:

It should be noted that for any useful organo-silicon compound having two silicon atoms in the molecule, as illustrated in formula XII, the moiety chosen to derive a working parameter of solubility excludes silicon. Hence, for the formula XII compound the organo moiety is that portion of the group comprising the segment in the chain between the two silicon atoms.

It has also been found that organo-silane compounds having both a hydrolyzable group and an organo moiety attached to a silicon atom and which are observed to be substantially ineffective in improving the spraying, casting or molding properties of magnesia compositions can be made effective by reacting the organo-silane compounds with epoxide-containing compounds. For example, while both ureidopropyltriethoxysilane (A-1160; Union Carbide) and mercaptoethyltriethoxysilane (A-1893; Union Carbide) perform poorly in lowering the viscosities of magnesia compositions, the reaction products of the silanes with 1,2-butylene oxide are effective in lowering magnesia composition viscosities, which reaction products are comprised, respectively, of compounds believed to have the structures of formulae XIII and XIV:

A working parameter of solubility, $\delta_{wp}$, for an organo moiety of each of the illustrated organo-silanol salts and organo-silicon compounds may be derived by inserting the molar attraction and molar volume constants of Table I into the aforementioned expression of the working parameter of solubility. A typical example of the calculation, as derived for the organo-silicon compound for formula XIV, would be as follows:

| Organo moiety chemical groups | —CH$_2$— —CH$_2$— —S— —CH$_2$— —CH— —OH —CH$_2$— —CH$_3$ |
|---|---|
| $\Sigma F_i$ | = 4(131.5) + 209.4 + 86.0 + 225.8 + 148.3 |
| | = 1195.5 |
| $\Sigma V_i$ | = 4(21.8) + 21.6 + 13.6 + 14.9 + 27.8 |
| | = 165.1 |
| $\delta_{wp} = \dfrac{\Sigma F_i}{\Sigma V_i}$ | = $\dfrac{1195.5}{165.1}$ = 7.24 |

The working parameters of solubility for the other compounds depicted in the formulae I through XIII, derived as shown in the aforementioned example, are listed in Table II. Experimental results as reported in the following working examples and in the examples of the aforementioned copending application indicate a crucial range of values of working parameters of solubility. Within this range are included the depicted organo-silicon compounds, both organo-silanes and organo-silanol salts, that are known to provide improved castable, moldable, or sprayable cementitious magnesia compositions.

TABLE II

| Structural Formula | Organo Moiety Working Parameter of Solubility, $\delta_{wp}$ (cal./c.c.)$^{\frac{1}{2}}$ |
|---|---|
| VIII | 6.41 |
| VII | 6.74 |
| X | 6.95 |
| XI | 7.02 |
| I, III | 7.19 |
| IX | 7.21 |
| XIV | 7.24 |
| V | 7.33 |
| II, IV | 7.36 |
| XIII | 7.43 |
| XII | 7.52 |
| VI | 7.83 |

Base hydrolysis of each of the described organo-silanes of formulae III through XIV under conditions similar to those for forming the silanol salts of formulae I and II, may provide organo-silanol salts characterized in having at least one salt group having the formula $-O^-A^+$, where $A^+$ is a monovalent cation or its electrical equivalent, as defined above. It is believed that these organo-silanol salts when incorporated in magnesia compositions provide materials having improved casting, molding or spraying properties.

Figure 1:
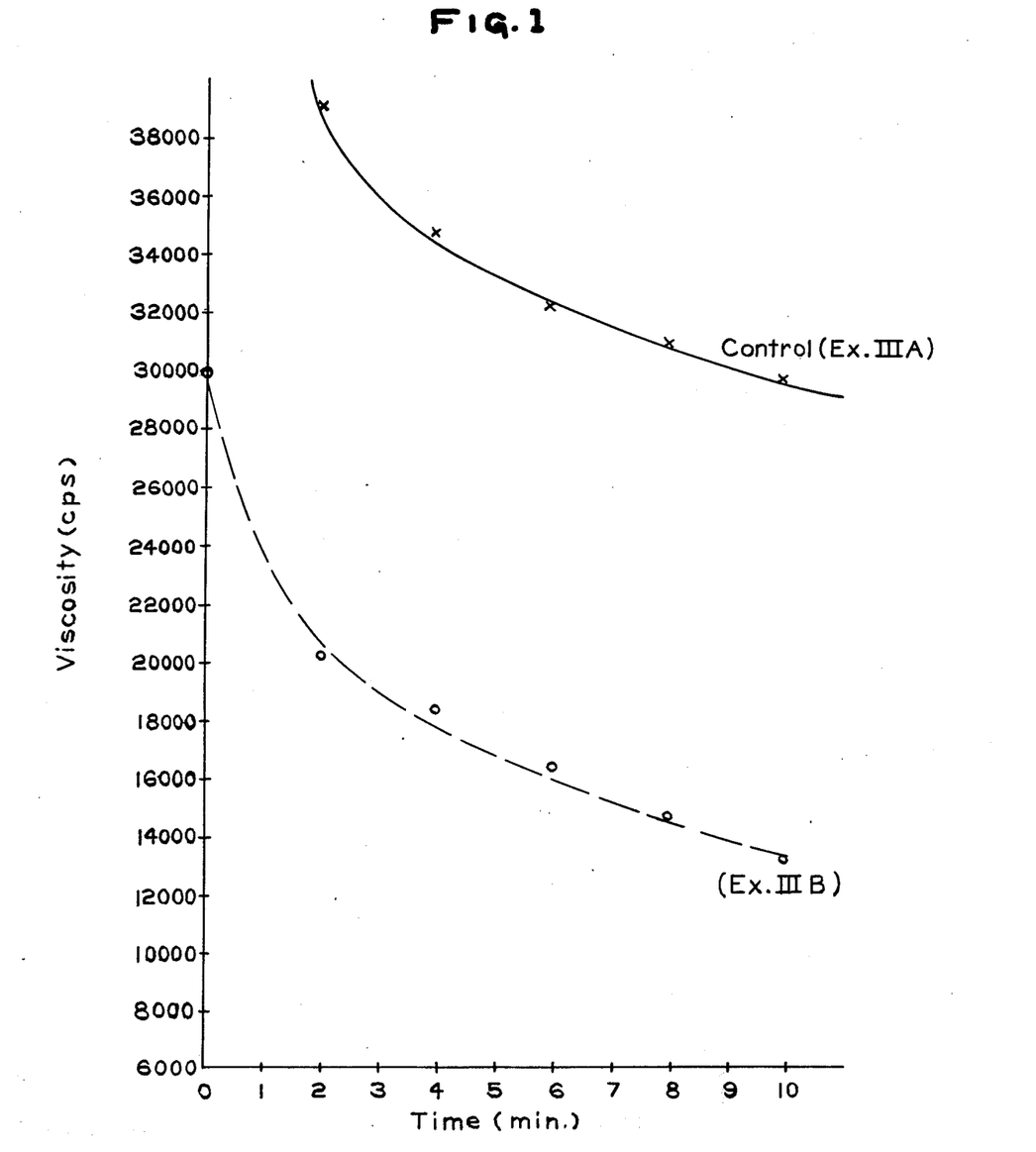
Figure 2:
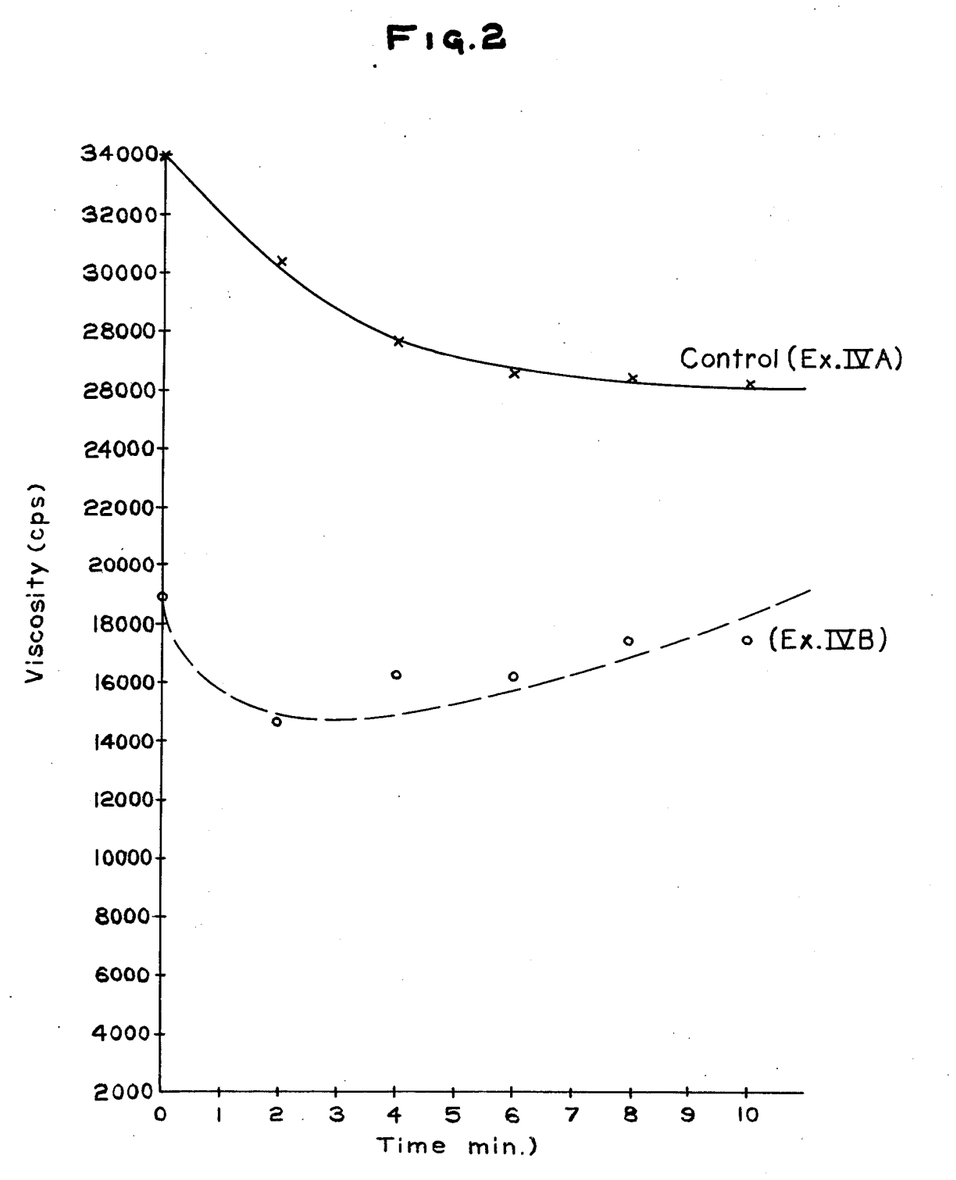

It should be noted that in utilization of the organo-silanol salts in magnesia compositions of the working examples, there is observed varying degrees of improvement in the casting, molding or spraying properties of the resulting cementitious magnesia compositions. The data derived from the working examples are reported in Table III, with the graphs of FIGS. 1 and 2 illustrating viscosity profiles of working embodiments of the invention. "Improvement" is identified as a measurable net lowering of the viscosities of "test" magnesia compositions having the organo-silanol salt additive in comparison to changes in the viscosities of "control" magnesia compositions lacking the additive. Viscosity measurements are taken just after preparation of the composition ("0 minute") and at intervals on a Brookfield LVT viscometer equipped with a No. 4 spindle rotating at 12 r.p.m., with rotation of the spindle being maintained during the test period. Test magnesia compositions determined as providing improved properties are those which show a lower viscosity than the control at some initial measuring point and at one or more of the other measuring points during the test period.

Improvements in application properties of preferred magnesia compositions containing organo-silanol salt additives are demonstrated by the viscosity profile data of FIGS. 1 and 2. Some organo-silanol salt containing magnesia compositions show reduced viscosities for a short period of time, which reductions are followed by rather rapid increases in viscosity, such as shown by the composition of Example IV B in FIG. 2. These sharp increases are believed attributable to some organo-silanol salts exerting an accelerating effect on cure of the compositions. Magnesia compositions having short viscosity reduction periods would be useful in spraying applications where an initial viscosity reduction is beneficial in forcing the cementitious material through spray device orifices, and where rapid setting of the sprayed material on a vertical substrate such as a wall is necessary to keep the material from sagging.

On the other hand, some magnesia compositions containing an organo-silanol salt additive have viscosity reduction periods of ten minutes or more, such as shown by the composition of Example III B in FIG. 1. These compositions are quite useful for molding applications where it may be necessary to provide an extended period of time during application of the composition for a desired use, or to store a change of the prepared, wet cementitious composition for some time before it is molded.

Cementitious magnesia compositions may have one or more of the described organo-silanol salts in an amount in the range from about 0.5 percent to 10 percent or more by weight of the magnesium oxide in the composition. Preferably, the organo-silanol salts are present in an amount in the range of about 2 to about 5 percent. A high percentage by weight of the organo-silanol salt component in the cementitious composition is generally not desirable because of the relatively high cost of the component.

The compositions are usually formulated by dissolving one or more water-soluble magnesium salts in an amount of water sufficient to form a saturated or nearly saturated solution in a mixing vessel. Then in a separate vessel, such as a Patterson-Kelly mixer, organo-silanol salt is blended with the water-insoluble magnesium oxide. The blend is then added to the magnesium salt-in-water solution with stirring to obtain a homogeneous slurry.

The magnesium compositions are usable as described for casting articles in a mold form, with or without the use of compression or heat, and for sprayapplying onto a substrate. The compositions typically are in a slurry state when placed in the mold to form an article, and then the article is removed as soon as the composition cures sufficiently to a rigid state so that the molded article can be handled without any adverse effects. The cured article then will typically undergo an aging process with an increase in strength and hardness usually occurring.

It has been found that the compositions of the invention can be formulated in a two-package, storage stable system which in the presence of water forms a moldable and castable cementitious material of pourable consistency. The two-package system comprises a first composition which includes at least one magnesium salt having at least moderate solubility in water. A second composition of the two-package system is prepared from mixing together magnesium oxide and a water-soluble organo-silanol salt of the aforementioned type. The first and second compositions may be mixed with sufficient water just prior to use to form a cementitious composition that is curable to a hardened article.

The first composition of the two-package system can comprise the magnesium salt, or salts, alone; or the first composition may have one or more magnesium salts of any of the aforementioned type dissolved in an amount of water effective to form a saturated or nearly saturated solution of the magnesium salt or salts. In either case, the first composition is sufficiently stable to satisfy most commercial or industrial storage conditions and shelf-life requirements.

The second composition is prepared by blending the water-soluble silanol salt in a Patterson-Kelly mixer as described above. It is believed any of the aforementioned general classes of silanol salts may be blended with magnesium oxide in the mole ratios set forth above and that these blends form stable compositions storable for lengths of time and under conditions typical for most of the contemplated uses.

Two-package systems for forming cementitious compositions of the invention are quite useful inasmuch as the blending of the magnesium oxide and silanol salt components can be closely controlled by use of elaborate and expensive mixing equipment which may not be available to end users of the compositions. The two-package system has the further advantage of requiring only one mixing step by the ultimate user which thereby enhances the convenience of use of the compositions and ensures the optimum ratio of components in the material for molding, casting and spraying uses.

Quite often, magnesia compositions of the described formulations contain additional materials to increase the cure rate, to increase wet or dry strength, to reduce shrinkage, to prevent cracking, or to reduce water sensitivity of the cured composition.

Additives to increase the wet strength, or to improve the strength or crack resistance of the cured composition include materials such as fibrous glass, sisal, mineral wool, mica and cotton, each of which may be present in mat or chopped form. Typically, these materials are present in an amount in a range from about 1 to about 50 percent by weight of the cured composition, and preferably from about 5 to about 30 percent.

There may be surfactants present in the cementitious compositions to improve spreadability of the compositions in the wet form. Examples of such additive include non-ionic surfactants which may be present in an amount sufficient to reduce the surface tension of the uncured composition; usually surfactants are present in an amount in a range from about 0.1 to about 5 percent by weight of the wet composition.

Other useful additives which may be included in the magnesia compositions, especially for compositions utilized for molding purposes, are thickening agents, fillers and mold release agents. Thickening agents, which serve to maintain uniform consistency in the wet composition matrix, include hydroxyethyl cellulose, hydroxypropyl cellulose, polyethylene oxide and polyvinyl alcohol. Examples of fillers are clays, talc and calcium carbonate. Suitable mold release agents include "Zelec UN" (DuPont), zinc stearate, aluminum stearate and various lubricating silicone compounds. When used, these additives may be present in an amount in the range of about 0.01 to about 5 weight percent based on total weight of the wet composition.

Coloring pigments or water-soluble dyes may also be present in the compositions. Typical coloring pigments include iron oxides, cadmium sulphide, carbon black, phthalocyanine blue, phthalocyanine green, ultramarine blue, chromium oxide, burnt umber, benzidine yellow, toluidine red and aluminum powder. When used, the pigments or dyes may be present in an amount in the range of about 0.1 to about 10 weight percent based on total weight of the wet composition.

When any of the aforementioned additives are to be included in the cementitious compositions, the additives may be introduced during any one of the composition preparation stages. In the two-package system it is preferred that additives in a water base be included in the first composition of the system, that is, in the composition containing one or more of the magnesium salts.

The following examples set forth specific embodiments of the invention. However, the invention is not to be construed as being limited to these embodiments for there are, of course, numerous possible variations and modifications. All parts and percentages of the examples as well as throughout the specification are by weight unless otherwise indicated.

EXAMPLE I

Into a reaction vessel equipped with agitating means, heating means, a thermometer and refluxing means and containing 500 parts distilled water, there is slowly added 168 parts potassium hydroxide with mixing to obtain a clear solution. Then 221 parts γ-aminopropyltriethoxysilane is slowly added to the reaction vessel with continued stirring of the vessel contents. The reaction mixture is refluxed for 30 minutes. The reaction vessel is then fitted with distillation means. Heating continues with collection of liquid distillate until a vapor distillate temperature of 100° C. is attained, at which time the reaction mixture is allowed to cool. Of the 151 parts distillate collected, approximately 95 percent consists of ethanol. The reaction mixture comprises one or more of the mono-, di-, or tri-potassium salts of the amino silanol formed from the hydrolysis of γ-aminopropyltriethoxysilane.

EXAMPLE II

Into a reaction vessel equipped as in Example I and containing approximately 706 parts distilled water, there is slowly added 168 parts potassium hydroxide with mixing to obtain a clear solution. Then 222 parts N-β-aminoethyl-γ-aminopropyltrimethoxysilane is added slowly to the vessel contents with continued stirring. The reaction mixture is refluxed at about 78° C. for 30 minutes. The reaction vessel is then fitted with distillation means. Heating continues with collection of liquid distillate until a vapor distillate temperature reaches 94° C., at which time the reaction mixture is allowed to cool. Approximately 121 parts distillate is collected consisting of about 95 percent ethanol. The reaction mixture comprises one or more of the mono-, di- or tri-potassium salts of the amino silanol formed from the hydrolysis of N-β-aminoethyl-γ-aminopropyltrimethoxysilane.

EXAMPLE III

Into a mixing vessel there is charged 400 parts water together with 688 parts magnesium chloride hexahydrate. Mixing proceeds until the magnesium chloride is completely dissolved in water. Then 1020 parts magnesium oxide is added to the vessel and mixing proceeds just long enough to obtain a smooth uniform blend, with care being taken so that excessive heat is not generated. A portion of the composition is then immediately placed into a Brookfield LVT viscometer vessel equipped with a No. 4 spindle rotated at 12 r.p.m. Viscosity readings on this composition "A", designated as "control", are taken at regular intervals. A second composition, designated test composition "B", is prepared by introducing 1020 parts magnesium oxide into a Patterson-Kelly blender equipped with a liquid feed device in the intensifier bar. Through the liquid feed device there is charged 95.9 parts of a water solution containing 33.7 parts of the potassium salt of the amino silanol derived from γ-aminopropyltriethoxysilane, prepared as in Example I. Mixing continues until a homogeneous blend is obtained. In a mixing vessel there is charged 688 parts magnesium chloride hexahydrate together with 400 parts water. Mixing proceeds to achieve a homogeneous solution. Then the contents of the Patterson-Kelly mixer are added to the previously prepared magnesium chloride-in-water solution with sufficient mixing to obtain a homogeneous blend. Viscosity readings are taken immediately upon preparation of the blend and at regular subsequent intervals. Comparative viscosity data of compositions "A" and "B" are shown in Table III and FIG. 1.

EXAMPLE IV

Into a mixing vessel there is charged 400 parts water together with 688 parts magnesium chloride hexahydrate. Mixing proceeds until the magnesium chloride is completely dissolved in the water. Then 1020 parts magnesium oxide is added to the vessel and mixing proceeds just long enough to obtain a smooth uniform blend, with care being taken so that excessive heat is not generated. A portion of the composition is then immediately placed into a Brookfield LVT viscometer vessel equipped with a No. 4 spindle rotated at 12 r.p.m. Viscosity readings on this composition "A", designated as "control", are taken at regular intervals. A second composition, designated test composition "B", is prepared by introducing 1020 parts magnesium oxide into a Patterson-Kelly blender equipped with a liquid feed device in the intensifier bar. Through the liquid feed device there is charged 95.9 parts of a water solution containing 33.7 parts of the potassium salt of the amino silanol derived from N-β-aminoethyl-γ-aminopropyltrimethoxysilane prepared as in Example II. Mixing continues until a homogeneous blend is obtained. In a mixing vessel there is charged 688 parts magnesium chloride hexahydrate together with 400 parts water. Mixing proceeds to achieve a homogeneous solution. Then the contents of the Patterson-Kelly mixer are added to the previously prepared magnesium chloride-in-water solution with sufficient mixing to obtain a homogeneous blend. Viscosity readings are taken immediately upon preparation of the blend and at regular subsequent intervals. Table III and FIG. 2 show comparative viscosity data of compositions "A" and "B".

liquid phase. Mixing proceeds vigorously for as short a period of time as possible to obtain a composition having a smooth, creamy consistency. Into a mold designed to form a panel six inches square and about 0.1 inch thick, there are placed a one-ply layer of commercially available finely-spun fiber glass veil mat, two plies of continuous-strand fiber glass mat, a charge of the wet molding composition sufficient to fill the mold and an overlay of one-ply fiber glass veil mat. The mold parts are closed, a mold compressive force of 100 psi is applied with a mold temperature of about 121° C. maintained for about three minutes. The mold is opened and an acceptably cured panel is removed that is observed to have a hard surface upon handling.

Although specific examples of the instant invention have been set forth hereinabove, it is not intended that the invention be limited solely thereto, but is to include all the variations and modifications falling within the scope of the appended claims.

What is claimed is:
1. A moldable, castable or sprayable cementitious composition, comprising:
    (a) magnesium oxide;
    (b) a magnesium salt having at least moderate solubility in water;
    (c) at least one water-soluble organo-silanol salt, characterized in having attached to the silicon atom (i) at least one group comprising a water-soluble salt having the general formula:

$$O^- A^+$$

where $A^+$ is a monovalent cation or one equivalent of a polyvalent cation and (ii) at least one group comprising an organo moiety attached to the silicon atom through a substantially non-hydrolyzable silicon-carbon bond with the organo moiety further characterized in having a working parameter

TABLE III

| Example No. | Composition (control) | (test) | Viscosity Readings (cps.)* | | | | | |
|---|---|---|---|---|---|---|---|---|
| | | | @0 min. | @2 min. | @4 min. | @6 min. | @8 min. | @10 min. |
| III | A | | 38,000 | 39,250 | 34,750 | 32,250 | 31,000 | 29,750 |
| | | B | 30,000 | 20,250 | 18,500 | 16,500 | 14,750 | 13,250 |
| IV | A | | 34,000 | 30,500 | 27,750 | 26,750 | 26,500 | 26,250 |
| | | B | 19,000 | 14,750 | 16,250 | 16,250 | 17,500 | 17,500 |

*Viscosity readings taken on Brookfield LVT viscometer equipped with a No. 4 spindle rotating at 12 r.p.m.; rotation of spindle was maintained during entire test period.

EXAMPLE V

Into a mixing vessel there is charged 400 parts water, together with 688 parts magnesium chloride hexahydrate. Mixing continues until a thoroughly homogeneous solution is obtained, after which time this "liquid phase" is allowed to age for several hours.

Into a Patterson-Kelly blender equipped with a liquid feed device in the intensifier bar, there is charged 1020 parts magnesium oxide. Through the liquid feed device there is charged 95.9 parts of a water solution containing 33.7 parts of the potassium salt of the amino silanol derived from γ-aminopropyltriethoxysilane prepared as in Example I. Mixing is continued until a homogeneous blend is obtained. Then 52 parts of a polyvinylchloride resin is added to the vessel, followed by continuous mixing to obtain a uniform mixture known as a "dry blend".

A wet molding composition to be used immediately is prepared by bringing together the dry blend and the of solubility, $\delta_{wp}$, in the range of about 6.2 to about 8.0 (cal./c.c.)$^{\frac{1}{2}}$, with $$\delta_{wp} = \frac{\Sigma F_i}{\Sigma V_i}$$

wherein:
    $F_i$ = the molar attraction constant of an individual functional group of said moiety expressed in (cal. c.c.)$^{\frac{1}{2}}$ per mole, and
    $V_i$ = the molar volume constant of an individual group of said moiety expressed in c.c. per mole; and
    (d) a liquid phase comprising water;
wherein the mole ratio of the magnesium oxide to the magnesium salt ranges from 3:1 to 10:1, the level or organo-silanol salt ranges from about 0.5 percent to about 10 percent by weight of the magnesium oxide and the level of water is in an amount effective to cause reaction of at least a portion of said magnesium oxide and at least a portion of said magnesium salt to form a matrix curable to a hardened state.

2. The cementitious composition of claim 1, wherein said magnesium salt is selected from the group consisting of magnesium chloride, hydrated magnesium chloride, magnesium sulphate, hydrated magnesium sulphate, hydrated magnesium nitrate, hydrated magnesium acetate, magnesium bromide and hydrated magnesium bromide.

3. The cementitious composition of claim 1, wherein said monovalent cation is selected from the group consisting of tertiary sulphonium, ammonium, substituted ammonium, quaternary ammonium and quaternary phosphonium.

4. The cementitious composition of claim 1, wherein said monovalent cation is selected from the group consisting of Group IA alkali metal cations.

5. The cementitious composition of claim 1, wherein said organo-silanol is a hydrolyzate of an organo-silicon compound, said organo-silicon compound characterized in having attached to its silicon atom one or two groups having a hydrolyzable bond with the silicon atom and selected from the group consisting of alkoxyl, aryloxyl, substituted aryloxyl, aralkoxy, substituted aralkoxyl, alylamino, substituted alkylamino, silylamino, substituted silylamino, mercapto and substituted mercapto.

6. The cementitious composition of claims 1 or 5, wherein said organo moiety comprises alkyl or oxalkyl group which may be substituted with one or more groups selected from the group consisting of alkyl, alkoxy, aryl, aryloxy, substituted aryloxy, acrylyl, substituted acrylyl, carboxy, carboalkoxy, amino, amido, ureido, oxiranyl and sulphur.

7. The cementitious composition of claim 5, wherein said organo-silicon compound is a reaction product of a compound containing acrylyl or substituted acrylyl groups and a silane having an organo moiety comprising an amino group containing at least one active hydrogen.

8. The cementitious composition of claim 5, wherein said organo-silicon compound is a reaction product of an amino-compound having at least one active hydrogen and a silane having an organo moiety comprising acrylyl or substituted acrylyl groups.

9. The cementitious composition of claim 5, wherein said organo-silicon compound is a reaction product of an silane having an organo moiety containing an epoxy group and a compound containing a chemical group selected from the group consisting of amino, amide, ureido, urea, urethane, thiol and hydroxyl, each having at least one active hydrogen atom.

10. The cementitious composition of claim 5, wherein said organo-silicon compound is a reaction product of an epoxy-containing compound and a silane having an organo moiety comprising one or more chemical groups selected from the group consisting of primary amino, secondary amino, amide, urea, urethane and thiol, each having at least one active hydrogen atom.

11. The cementitious composition of claim 10, wherein said epoxycontaining compound is an aliphatic epoxide and said silane is an aminoalkylsilane.

12. The cementitious composition of claim 11, wherein said aliphatic epoxide is 1,2-butylene oxide and said aminoalkylsilane is γ-aminopropyltriethoxysilane.

13. The cementitious composition of claim 11, wherein said aliphatic epoxide is 1,2-butylene oxide and said aminoalkylsilane is N-β-aminoethyl-γ-aminopropyltrimethoxysilane.

14. The cementitious composition of claim 10, wherein said epoxy-containing compound is 1,2-butylene oxide and said silane is ureidopropyltriethoxysilane.

15. The cementitious composition of claim 10, wherein said epoxy-containing compound is an aliphatic epoxide and said silane is a thioalkyl silane.

16. The cementitious composition of claim 15, wherein said aliphatic epoxide is 1,2-butylene oxide and said thioalkyl silane is mercaptoethyltriethoxysilane.

17. The cementitious composition of claim 10, wherein said epoxy-containing compound is an aliphatic polyepoxide and said silane is an aminoalkylsilane.

18. The cementitious composition of claim 17, wherein said aliphatic polyepoxide is 1,4-butanediol di-glycidyl ether and said aminoalkylsilane is γ-aminopropyltriethoxysilane.

19. The cementitious composition of claim 5, wherein said organo-silicon compound has the structure:

$$CH_3O-\underset{\underset{OCH_3}{|}}{\overset{\overset{OCH_3}{|}}{Si}}-CH_2CH_2CH_2O\overset{\overset{O}{\|}}{C}\underset{\underset{CH_3}{|}}{C}=CH_2$$

20. The cementitious composition of claim 5, wherein said organo-silicon compound has the structure:

$$CH_3O-\underset{\underset{OCH_3}{|}}{\overset{\overset{OCH_3}{|}}{Si}}-CH_2CH_2CH_2OCH_2\overset{\overset{O}{/\backslash}}{CH}CH_2$$

21. The cementitious composition of claim 5, wherein said organo-silicon compound has the structure:

$$CH_3CH_2O-\underset{\underset{OCH_2CH_3}{|}}{\overset{\overset{CH_3}{|}}{Si}}-CH_2CH_2CH_2NH_2$$

22. The cementitious composition of claim 5, wherein said organo-silicon compound has the structure:

$$CH_3O-\underset{\underset{CH_3}{|}}{\overset{\overset{CH_3}{|}}{Si}}-CH_2CH_2CH_2CH_2NH_2$$

23. The cementitious composition of claim 1, wherein said organo-silanol salt has the structure:

$$^+K-O-\underset{\underset{O^-K^+}{|}}{\overset{\overset{O^-K^+}{|}}{Si}}-CH_2CH_2CH_2NH_2$$

24. The cementitious composition of claim 1, wherein said organo-silanol salt has the structure:

25. The cementitious composition of claim 1 further comprising a material selected from the group consisting of fibrous glass, sisal, mica, mineral wool and cotton.

26. The cementitious composition of claim 1 further comprising a thickening agent selected from the group consisting of hydroxyethyl cellulose, hydroxypropyl cellulose, polyethylene oxide and polyvinyl alcohol.

27. The cementitious composition of claim 1 wherein the mole ratio of magnesium oxide to the magnesium salt ranges from 6:1 to 7.5:1 and the level of organo-silanol salt in the composition ranges from about 2 percent to about 5 percent by weight of the magnesium oxide.

28. A process for forming an article from a curable cementitious composition, comprising:
(a) mixing together in the presence of a liquid phase having water sufficient to produce a moldable, curable slurry composition, the components of:
(1) magnesium oxide;
(2) at least one magnesium salt having moderate solubility in water; and
(3) at least one water-soluble organo-silanol salt, characterized in having attached to the silicon atom (i) at least one group comprising a water-soluble salt having the general formula:

$$O-A^+$$

where $A^+$ is a monovalent cation or one equivalent of a polyvalent cation and (ii) at least one group comprising an organo moiety attached to the silicon atom through a substantially non-hydrolyzable silicon-carbon bond with the organo moiety further characterized in having a working parameter of solubility, $\delta_{wp}$, in the range of about 6.2 to about 8.0 (cal.c.c.)$^{\frac{1}{2}}$, with $$\delta_{wp} = \frac{\Sigma F_i}{\Sigma V_i}$$

wherein:
$F_i$=the molar attraction constant of an individual functional group of said moiety expressed in (cal.c.c.)$^{\frac{1}{2}}$ per mole, and
$V_i$=the molar volume constant of an individual group of said moiety expressed in c.c. per mole; and wherein the mole ratio of the magnesium oxide to the magnesium salt ranges from 3:1 to 10:1, the level of organo-silanol salt ranges from about 0.5 percent to about 10 percent by weight of the magnesium oxide
(b) placing said slurry composition in a mold form; and
(c) allowing said composition to cure sufficiently such that said article may be removed from the mold form without substantially adversely affecting the integrity of the molded article.

29. The process of claim 28, wherein said components are mixed together by (a) firstly, preparing a blend of said magnesium oxide and said organo-silanol salt; and
(b) subsequently mixing said blend with said magnesium salt in the presence of said water.

30. The process of claim 28 further comprising introducing into said slurry composition a material selected from the group consisting of fibrous glass, sisal, silicas, mica, mineral wool and cotton.

31. The process of claim 28 further comprising forming said article with the aid of compression force of heat, or both.

32. The process of claim 28, wherein said magnesium salt is selected from the group consisting of mangesium chloride, hydrated magnesium chloride, magnesium sulphate, hydrated magnesium sulphate, hydrated magnesium nitrate, hydrated magnesium acetate, magnesium bromide and hydrated magnesium bromide.

33. The process of claim 28, wherein said monovalent cation is selected from the group consisting of tertiary sulphonium, ammonium, substituted ammonium, quaternary ammonium, quaternary phosphonium and Group IA alkali metal cations.

34. The process of claim 28, wherein said organo moiety of said organo-silanol comprises alkyl group which may be substituted with one or more groups selected from the group consisting of alkyl or alkoxyl groups of one to about eight carbon atoms, primary amino group and secondary amino group.

35. The process of claim 28, wherein said organosilanol is a hydrolyzate of an organo-silicon compound, said organo-silicon compound characterized in having attached to its silicon atom one or two groups having a hydrolyzable bond with the silicon atom and selected from the group consisting of alkoxyl, aryloxyl, substituted aryloxyl, aralkoxyl, substituted aralkoxyl, alkylamino, substituted alkylamino, silylamino, substituted silylamino, mercapto and substituted mercapto.

36. The process of claims 28 or 35 wherein said organo moiety comprises alkyl or oxalkyl group which may be substituted with one or more groups selected from the group consisting of alkyl, alkoxy, aryl, aryloxy, substituted aryloxy, acrylyl, substituted acrylyl, carboxy, carboalkoxy, amino, amido, ureido, oxiranyl and sulphur.

37. The process of claim 35, wherein said organo-silicon compound is a reaction product of a compound containing acrylyl or substituted acrylyl groups and a silane having an organo moiety comprising an amino group containing at least one active hydrogen.

38. The process of claim 35, wherein said organo-silicon compound is a reaction product of an amino-compound having at least one active hydrogen and a silane having an organo moiety comprising acrylyl or substituted acrylyl groups.

39. The process of claim 35, wherein said organo-silicon compound is a reaction product of a silane having an organo moiety containing an epoxy group and a compound containing a chemical group selected from the group consisting of amino, amide, ureido, urea, urethane, thiol and hydroxyl, each having at least one active hydrogen.

40. The process of claim 35, wherein said organo-silicon compound is a reaction product of an epoxy-containing compound and a silane having an organo moiety comprising one or more chemical groups selected from the group consisting of primary amino, secondary amino, amide, urea, urethane and thiol, each having at least one active hydrogen atom.

41. The process of claim 40, wherein said epoxy-containing compound is an aliphatic epoxide and said silane is an aminoalkylsilane.

42. The process of claim 35, wherein said organo-silicon compound is selected from the group consisting of compounds illustrated by the formulae:

43. The process of claim 35, wherein said organo-silicon compound is seleced from the group consisting of
(a) a reaction product of 1,2-butylene oxide and γ-aminopropyltriethoxysilane;
(b) a reaction product of 1,2-butylene oxide and ureidopropyltriethoxysilane;
(c) a reaction product of 1,2-butylene oxide and mercaptoethyltriethoxysilane; and
(d) a reaction product of 1,4-butanediol diglycidyl ether and γ-aminopropyltriethoxysilane.

44. The process of claim 28, wherein said organo-silanol salt has the structure:

45. The process of claim 28, wherein said organo-silanol salt has the structure:

46. The process of claim 28 wherein the level of the magnesium oxide to the magnesium salt ranges from 6:1 to 7.5:1 and the level of the organo-silanol salt ranges from about 2 percent to about 5 percent by weight of the magnesium oxide.

47. A product produced by the process of claim 28.

48. A storage stable two-package system for forming in the presence of water a moldable, castable or sprayable cementitious material when a first composition is mixed with a second composition, comprising:
(a) said first composition including at least one magnesium salt having at least moderate solubility in water; and
(b) said second composition prepared from mixing together
(1) magnesium oxide; and
(2) at least one water-soluble organo-silanol salt, characterized in having attached to the silicon atom (i) at least one group comprising a water-soluble salt having the general formula:

$$O^- A^+$$

where $A^+$ is a monovalent cation or one equivalent of a polyvalent cation and (ii) at least one group comprising an organo moiety attached to the silicon atom through a substantially nonhydrolyzable silicon-carbon bond with the organo moiety further characterized in having a working parameter of solubility, $\delta_{wp}$, in the range of about 6.2 to about 8.0 (cal./c.c.)$^{\frac{1}{2}}$, with $$\delta_{wp} = \frac{\Sigma F_i}{\Sigma V_i}$$

wherein:
$F_i$ = the molar attraction constant of an individual functional group of said moiety expressed in (cal. c.c.)$^{\frac{1}{2}}$ per mole, and
$V_i$ = the molar volume constant of an individual group of said moiety expressed in c.c. per mole; with the organo-silicon compound at a level ranging from about 0.5 percent to about 10 percent by weight of the magnesium oxide;
said compositions being mixed at time of use at levels to provide a mole ratio of the magnesium oxide to the magnesium salt of from about 3:1 to about 10:1.

49. The two-package system of claim 48, wherein said first composition further comprises water in an amount effective to form a saturated or nearly saturated solution with said magnesium salt.

50. The two-package system of claim 48, wherein said magnesium salt is selected from the group consisting of magnesium chloride, hydrated magnesium chloride, magnesium sulphate, hydrated magnesium sulphate, hydrated magnesium nitrate, hydrated magnesium acetate, magnesium bromide and hydrated magnesium bromide.

51. The two-package system of claim 48, wherein said monovalent cation is selected from the group consisting of tertiary sulphonium, ammonium, substituted ammonium, quaternary ammonium, quaternary phosphonium and Group IA alkali metal cations.

52. The two-package system of claim 48, wherein said organo moiety comprises alkyl group which may be substituted with one or more groups selected from the group consisting of alkyl of one to about eight carbon atoms, primary amino and secondary amino.

53. The two-package system of claim 48, wherein said organo-silanol is a hydrolyzate of an organo-silicon compound, said organo-silicon compound characterized in having attached to its silicon atom one or two groups having a hydrolyzable bond with the silicon atom and selected from the group consisting of alkoxyl, aryloxyl, substituted aryloxyl, aralkoxyl, substituted aralkoxyl, alkylamino, substituted alkylamino, silylamino, substituted silylamino, mercapto and substituted mercapto.

54. The two-package system of claims 48 or 53, wherein said organo moiety comprises alkyl or oxalkyl group which may be substituted with one or more groups selected from the group consisting of alkyl, alkoxy, aryl, aryloxy, substituted aryloxy, acrylyl, substituted acrylyl, carboxy, carboalkoxy, amino, amido, ureido, epoxy and sulphur.

55. The two-package system of claim 53, wherein said organo-silicon compound is a reaction product of a compound containing acrylyl or substituted acrylyl groups and a silane having an organo moiety comprising an amino group containing at least one active hydrogen.

56. The two-package system of claim 53, wherein said organo-silicon compound is a reaction product of an amino-compound having at least one active hydrogen and a silane having an organo moiety comprising acrylyl or substituted acrylyl groups.

57. The two-package system of claim 53, wherein said organo-silicon compound is a reaction product of a silane having an organo moiety containing an epoxy group and a compound containing a chemical group selected from the group consisting of amino, amide, ureido, urea, urethane, thiol and hydroxyl, each having at least one active hydrogen atom.

58. The two-package system of claim 53, wherein said organo-silicon compound is a reaction product of an epoxy-containing compound and a silane having an organo moiety comprising one or more chemical groups selected from the group consisting of primary amino, secondary amino, amide, urea, urethane and thiol, each having at least one active hydrogen atom.

59. The two-package system of claim 58, wherein said epoxy-containing compound is an aliphatic epoxide and said silane is an aminoalkylsilane.

60. The two-package system of claim 53, wherein said organo-silicon compound is selected from the group consisting of compounds illustrated by the formulae:

61. The two-package system of claim 53, wherein said organo-silicon compound is selected from the group consisting of (a) a reaction product of 1,2-butylene oxide and γ-aminopropyltriethoxysilane;
(b) a reaction product of 1,2-butylene oxide and ureidopropyltriethoxysilane;
(c) a reaction product of 1,2-butylene oxide and mercaptoethyltriethoxysilane; and
(d) a reaction product of 1,4-butanediol diglycidyl ether and γ-aminopropyltriethoxysilane.

62. The two-package system of claim 48, wherein said organosilanol salt has the structure:

63. The two-package system of claim 48, wherein said organosilanol salt has the structure:

64. The two-package system of claim 48, wherein at least one of said compositions further comprises a material selected from the group consisting of fibrous glass, sisal, silica, mica, mineral wool and cotton.

65. The two-package system of claim 48, wherein at least one of said compositions further comprises a thickening agent selected from the group consisting of hydroxyethyl cellulose, hydroxypropyl cellulose, polyethylene oxide and polyvinyl alcohol.

66. The two-package system of claim 48 wherein the level of the organo-silanol salt ranges from about 2 percent to about 5 percent by weight of the magnesium oxide.

* * * * *